United States Patent
Busted

(10) Patent No.: US 6,605,260 B1
(45) Date of Patent: Aug. 12, 2003

(54) APPARATUS AND A METHOD FOR STERILIZING A MEMBER

(76) Inventor: Tommy Busted, Lange Müllers Gade 25, Copenhagen Ø (DK), DK-2100

( * ) Notice: Subject to any disclaimer, the term of this patent is extended or adjusted under 35 U.S.C. 154(b) by 0 days.

(21) Appl. No.: 09/673,506

(22) PCT Filed: Apr. 16, 1999

(86) PCT No.: PCT/DK99/00214

§ 371 (c)(1),
(2), (4) Date: Dec. 8, 2000

(87) PCT Pub. No.: WO99/53966

PCT Pub. Date: Oct. 28, 1999

(30) Foreign Application Priority Data

Apr. 17, 1998 (GB) .............................................. 9808286
Jul. 21, 1998 (DK) .................................... 1998 00270 U

(51) Int. Cl.[7] ................................................ B01J 19/08
(52) U.S. Cl. .............................. 422/186.3; 422/186.07; 422/24
(58) Field of Search .......................... 422/186.3, 186.07, 422/24

(56) References Cited

U.S. PATENT DOCUMENTS

| | | | |
|---|---|---|---|
| 4,309,388 A | * | 1/1982 | Tenney et al. ................. 422/24 |
| 4,772,795 A | | 9/1988 | Sakurai et al. |
| 5,184,633 A | | 2/1993 | Langford |
| 5,185,532 A | | 2/1993 | Zabsky et al. |

FOREIGN PATENT DOCUMENTS

| | | |
|---|---|---|
| DE | 29 04 391 | 8/1980 |
| DE | 3440078 A1 | 5/1986 |
| DE | 37 19 860 | 11/1988 |
| EP | 0 277 505 | 8/1988 |
| EP | 0 493 372 | 7/1992 |
| EP | 0 826 378 | 3/1998 |
| FR | 2627086 | 8/1989 |
| WO | WO 89/10145 | * 11/1989 |
| WO | 96 20017 | 7/1996 |

OTHER PUBLICATIONS

JP 2252460, "Steriliser for hand piece used in dentistry", Oct. 11, 1990, pp. 1–3.
JP 6154299, "Dental sterilisation device", Jun. 3, 1994, pp. 1–3.
JP 6121803, "Sterilisation device for dentistry", May 6, 1994, pp. 1–3.

* cited by examiner

Primary Examiner—Kishor Mayekar
(74) Attorney, Agent, or Firm—Wenderoth, Lind & Ponack, L.L.P.

(57) ABSTRACT

An apparatus for sterilizing a member includes a housing with an enclosure defined therein, a source of ultraviolet light for illuminating the member, and an ozone source. A pump is connected to the ozone source to force the ozone to flow within the enclosure, and a heating device heats the ozone flow.

11 Claims, 7 Drawing Sheets

APPARATUS AND A METHOD FOR STERILIZING A MEMBER

This application is a 35 USC 371 National Stage of PCT/DK99/00214 filed Apr. 16, 1999.

FIELD OF THE INVENTION

The invention relates to an apparatus for sterilizing a member including equipment for surgery or medical examination, such as dental handpieces, endoscopes, or catheters. Furthermore, the invention relates to methods for sterilizing a member.

BACKGROUND OF THE INVENTION

After surgery or medical examination of a patient, the equipment used has to be sterilized so that the equipment does not transport any bacteria or virus from the patient to the next patient. Typically, the equipment is sterilized in an autoclave. The autoclave sterilizes outer surfaces of the equipment by subjecting the equipment to an atmosphere of saturated heated aqueous vapor at 120° C. and at a pressure of 2 atmospheres for 20–30 minutes, or for even longer time periods.

It is a disadvantage of an autoclave that repeated sterilization in the autoclave wears and tears on autoclaved members as most materials used for manufacture of such members show a low resistance to aqueous vapor at high temperatures and pressures. For example, members comprising optical components or components made of rubber or silicon can not be sterilized in an autoclave due to those components having a low resistance to the environment in an autoclave.

It is another disadvantage of sterilization in an autoclave that it often takes several minutes or up to one hour to obtain sterilization. Further, heating members in the autoclave also requires time for cooling the member to room temperature. Typically, surgeons or dentists do not have time to wait for their instruments to be autoclaved, and this means that such instruments are not autoclaved as often as may be desired.

DE 29 04 391 discloses an apparatus for sterilizing, such as dental or medical equipment, by use of a source of ultraviolet light and ozone. Members to be sterilized are positioned on shelves in a box. Ozone circulates within the box by convection generated by a heating arrangement.

DE 34 40 078 discloses an apparatus for sterilizing dental equipment. The equipment is sterilized by ultraviolet light provided in a sterilization housing. The equipment is positioned on a dental tray, the tray being vertically movable, so that the tray with the equipment may be moved vertically up and into the sterilization housing wherein an ultraviolet lamp is positioned.

SUMMARY OF THE INVENTION

It is an object of the present invention to provide an apparatus that is capable of sterilizing members, such as dental or medical instruments, in a short time, such as shorter than 5 minutes. Thus, users of the members may sterilize members frequently, for example after each individual treatment of a patient.

It is a further object of the present invention to provide a sterilization process that results in a shorter sterilization time than the known processes such as the autoclave sterilization.

It is another object of the present invention to provide an apparatus that is capable of sterilizing members that do not cause wear and tear on members to be sterilized.

These objects are achieved by an apparatus for sterilizing a member which, in a first aspect of the present invention, comprises a housing defining an enclosure therein for receiving and holding the member, and a first source of ultraviolet light for illuminating the member with ultraviolet light and which is positioned in the enclosure.

According to the invention, the sterilization of a member is performed by positioning the member in the enclosure defined by the housing. In the enclosure, the first source of ultraviolet light is positioned for illumination of the member. Wall parts of the enclosure may be shaped to increase the intensity of ultraviolet light illuminating the member to be sterilized. The wall parts may have surfaces that reflect ultraviolet light, whereby the ultraviolet light illuminates the entire surface area of the member.

Micro organisms are killed by ultraviolet light since such light breaks DNA strings in the organism. The killing efficiency of the ultraviolet light depends on its wavelength. It has been found that, preferably, the wavelength of the ultraviolet light ranges from 249 to 259 nm, preferably from 250 to 258 nm or from 251 to 257 nm, or more preferably from 252 to 256 nm or from 253 to 255 nm, and most preferably approximately 253.7 nm.

In a preferred embodiment of the invention, the apparatus may further comprise an ozone source for generating ozone to be brought into contact with surfaces. For example, ozone may contact internal surfaces of a member that are not illuminated by the ultraviolet light, for sterilization of the contacted surfaces.

The apparatus may further comprise a pump connected to the ozone source for generation of a forced ozone flow within the enclosure, and a holding component positioned in the enclosure and adapted to receive and hold the member. Preferably, the holding component is connected to the pump so that the ozone flow passes over internal surfaces of the member. Thus, internal surfaces of the member that are not illuminated by the ultraviolet light for sterilization of the contacted surfaces are sterilized by ozone. The ozone has a chemical structure that is toxic and kills micro organisms within a short time.

The pump forces a flow of atmospheric air or oxygen into the ozone generating source, and after the air or oxygen has passed the ozone generator, the ozone is blown into the enclosure and into internal conduits of the member. The pump may blow atmospheric air or oxygen into the ozone generator or may draw air with ozone from the ozone generator. However, in a preferred embodiment, the pump blows atmospheric air or oxygen into the ozone generator so that ozone does not enter the pump.

When sterilizing a member in the enclosure, the member may be positioned in the enclosure on shelves, hanging on wires, etc. However, in a preferred embodiment of the present invention, the apparatus further comprises holding component positioned in the enclosure and adapted to receive and hold the member. The holding component may be a plate having apertures for receiving the members to be sterilized. In a preferred embodiment, the apertures may be positioned in a pipe stub that fits the member to be sterilized. The member is positioned over the pipe stub. The ozone flows through the stub and into internal conduits of the member. The connection between the ozone generator and the holding component may be provided by plastic tubes, rubber tubes, or steel tubes or any other type of tubes that are able to transport ozone.

The generation of ozone in the ozone source may be provided either by sparking in atmospheric air or by illuminating atmospheric air or oxygen with ultraviolet light. In a preferred embodiment, the apparatus comprises an ozone generator that includes its own source of ultraviolet light for generating ozone. By illumination of oxygen with ultraviolet light, oxygen is transformed into ozone. When passing a flow of atmospheric air or oxygen through the generator, the atmospheric air or oxygen is illuminated with ultraviolet light having a preferred wavelength that is particularly effective in transforming oxygen to ozone. The ozone may then be forced into the enclosure and into the internal parts of the member to be sterilized via the above-mentioned stubs.

For effective transformation of oxygen into ozone, the wavelength of the ultraviolet light preferably ranges from 179 to 189 nm, preferably from 180 to 188 nm, such as from 181 to 187 nm, more preferred from 182 to 186 nm, and even more preferred from 183 to 185 nm. It is presently most preferred that the wavelength is approximately 183.7 nm.

The apparatus may further comprise a heating device for heating the forced flow of ozone, so as to increase the activity of the ozone molecules and thereby provide an improved sterilization of surfaces (such as internal surfaces) of the member to be sterilized. The temperature of the heated flow ranges preferably from 40 to 80° C., more preferred from 50 to 70° C., and is most preferred approximately 60° C.

It is an important advantage of the present invention that the number of living micro organisms in a-member after sterilization in the apparatus is reduced by at least a factor of $10^6$. The determined reduction factor is in conformance with the international specification (Ph. Eur. 3rd. Ed. (1997) 2.6.1, Sterility) concerning sterilization of equipment. The apparatus is tested by sterilizing a member having been deliberately contaminated with the bacteria "*Bacillus subtilis var. niger*".

Furthermore, the apparatus may be able to disinfect a member, so that the number of micro organisms in the member after the disinfection is less than $10^5$ living micro organisms, less than $10^4$ living micro organisms, less than $10^3$ living micro organisms, less than $10^2$ living micro organisms, or most preferably less than 10 living micro organisms.

As mentioned above, the member being sterilized may be positioned on a holding component which may be positioned in the enclosure. To avoid any contacts after sterilization between the member to be sterilized and the surrounding atmosphere or the human operator, the member may be covered by a substantially sealed bag.

The bag for covering the member may be a closed bag with only one opening in the bottom, so that the bag may be pulled over the member from above before the member is introduced to the enclosure and positioned on the holding component. After sterilization, the member and the bag may be removed from the holding component. The opening in the bottom of the bag is provided with a closing device that will close the bag when it is removed from the holding component. The closing device may be any kind of spring loaded mechanism (like the closing device known from small wallets) which may be made of steel, plastic or rubber, pasty-like sealing, etc. The bag may be made of any kind of material that is penetrable by ultraviolet light.

Furthermore, the apparatus comprises an ozone neutralizing device for removing ozone so that ozone is prevented from leaving the apparatus and entering the surroundings of the apparatus. The ozone neutralizing device may comprise an active carbon filter facilitating transformation of ozone into oxygen. Ozone is not a stable molecule and interaction with the carbon atoms in the carbon filter causes ozone to be transformed into oxygen. The carbon filter may be connected to a fan that forces, e.g. draws, the ozone through the carbon filter.

The housing of the apparatus may be painted on its inner surfaces with an ozone neutralizing paint for further prevention of ozone leaving the enclosure and entering the surrounding area of the apparatus.

The sterilization process performed by the apparatus may be controlled manually or by a processor.

In a preferred embodiment, the apparatus further comprises a processor for controlling operation of the apparatus. The processor is adapted to control the first and second source of ultraviolet light and the pump, and is adapted to control the sterilization process. The processor may be adapted to perform different sterilization processes, each process being characterized by specific parameters, such as duration of illumination by the first ultraviolet light, duration of ozone treatment, etc, and is adapted to sterilize specific types of members.

According to a preferred embodiment of the invention, the processor is adapted to control the apparatus so that the first ultraviolet light source is turned on for approximately 30 seconds, the first ultraviolet light source is turned off, the ozone source is turned on for 30 seconds, and the ozone source is turned off, and ozone within the enclosure is transformed into oxygen to prevent emission of ozone to the surroundings of the apparatus.

It is an important advantage of the apparatus according to the present invention that sterilization of a member is provided within a short time, such as 3 min. Furthermore, the member is subjected to standard pressure and temperature (approximately 1 bar and 20° C.) during sterilization minimizing wear and tear of the member.

After completion of a sterilization cycle in the apparatus, ozone in the apparatus is eliminated before access to the enclosure by an operator of the apparatus is allowed. Ozone may be eliminated by transforming ozone into oxygen by recirculating air within the enclosure through the carbon filter, or by illuminating the enclosure by ultraviolet light having a wavelength causing transformation of ozone into oxygen, for example, by illumination by the first source of ultraviolet light.

A second aspect of the present invention relates to an apparatus for sterilizing a member. This apparatus comprises a source of ultraviolet light, a fibre optic probe, interface device at a first end of the fibre optic probe for enabling the fibre optic probe to receive the ultraviolet light such that the ultraviolet light is able to be transmitted along the fibre optic probe, and a cleaning head at a second end portion of the fibre optic probes.

The fibre optic probe and the cleaning head are adapted to sterilize the inside of the equipment.

The apparatus may be used for sterilizing any suitable and appropriate type of members. The apparatus can be used to sterilize parts of a member that are not easily accessible and that may not satisfactorily be cleaned by, for example, an autoclave. Usually, the cleaning head will have a cross sectional size which is substantially the same as the cross sectional size of the fibre optic probe. Generally, the cleaning head should be kept as narrow as possible, so that it is able to be inserted into small openings in the member to be cleaned.

In a preferred embodiment, the cleaning head includes a reflecting device for reflecting the ultraviolet light from the cleaning head. The reflecting device is able to increase the amount of ultraviolet light received in the inner parts being cleaned, and this may increase the speed of sterilization of the member that is sterilized in the apparatus according to this aspect of the present invention.

It the cleaning head includes the reflecting device, the apparatus may be one in which the fibre optic probe has an outer covering (in which the outer covering is removed at the cleaning head), and in which the reflecting device is in direct contact with each optical fibre in the fibre optic probe.

The reflecting device is preferably a plurality of small mirrors. Other types of reflecting device may be employed, so that the reflecting device can also be a single one-way mirror coating which is able to transmit the ultraviolet light and then reflect back the transmitted ultraviolet light. If the reflecting device comprises the plurality of small mirrors, then the mirrors are preferably made of polished steel. Other materials may, however, be employed.

Preferably, the fibre optic probe has only one optical fibre. If desired, however, the fibre optic probe may have more than one optical fibre, such as two, three, four or even five optical fibres.

The interface device may have an inverted T-shape. Other types of interface devices may however be employed.

The apparatus according to this second aspect of the invention may be in the form of a hand held instrument for effecting the sterilization of the member to be sterilized.

Preferably, the apparatus according to the second aspect of the invention may form part of a larger apparatus for also cleaning the outside of the member to be sterilized, such as the apparatus according to the first aspect of the invention. In this case, the apparatus may include a housing for receiving the member to be sterilized and a source of ultraviolet light for cleaning the outside of the member. The housing could be the one which is described in accordance with the first aspect of the invention or it could be any other housing.

The source of ultraviolet light for cleaning the outside of the member may be the source of ultraviolet light for the fibre optic probe, or may be a different source of ultraviolet light. Furthermore, the housing may comprise a holding component for holding the member to be sterilized.

The holding component may be a stand having apertures for receiving the member to be sterilized. Other types of holding components may be employed, such as the holding component in the first aspect of the present invention.

Furthermore, the apparatus according to the second aspect may comprise a source of ozone. The source of ozone may be in the form of a lamp which produces ozone, or the ozone could be generated by sparking in air. The lamp may be an ultraviolet lamp, but one which additionally produces ozone.

The first and second aspect of the present invention may be combined, so that the fibre optic probe is formed as an apparatus according to the first aspect of the invention. A combination provides an apparatus for sterilizing members, and which apparatus comprises all of the above-mentioned sterilizing components in one single apparatus, so that the apparatus comprises a housing which defines an enclosure, one or more ultraviolet light sources, one or more ozone generating sources such as ultraviolet light sources or sparking in air, one or more fibre optic probes, one or more pumps for generating a forced ozone flow within the enclosure and a ventilating grating comprising a fan and an active carbon filter. The ultraviolet light sources for illuminating the outer surfaces of the member and for the fibre optic probe may emit 25 light with a wavelength that ranges from 249 to 259 nm, and the ozone generating sources may emit ultraviolet light with a wavelength that ranges from 179 to 189 nm.

According to a third aspect of the invention, a method of sterilizing a member includes positioning a member in a housing defining an enclosure therein for receiving and holding the member, and turning on a first source of ultraviolet light which is positioned in the enclosure for illuminating the member with ultraviolet light for a first predetermined time interval.

The method of sterilizing a member may be carried out with different first predetermined time intervals, which depend on, for example, the size of the outer surface area and the type of contamination of the member to be sterilized. The first predetermined time interval may range from 10 to 60 seconds, preferably from 20 to 50 seconds, more preferred from 25 to 40 seconds, or even more preferred be approximately equal to 30 seconds.

The method may further comprise turning on, for a second predetermined time interval, a second source of ultraviolet light for generating ozone, and turning on a pump which is connected to the ozone source for generation of a forced ozone flow within the enclosure.

The method of sterilizing a member may be carried out with different first and second predetermined time intervals, which depend on, for example, the size of the outer and inner surface areas and the type of contamination of the member to be sterilized. The second predetermined time interval may range from 10 to 60 seconds, preferably from 20 to 50 seconds, more preferred from 25 to 40 seconds, or even more preferred be approximately equal to 30 seconds.

The steps in the method of sterilizing a member may be performed in another sequence other than the one disclosed above, and may comprise other values of the first and second predetermined time intervals. For example, the turning on of the first and second light source may be performed sequentially in any order or simultaneously, and the time intervals may be adjustable.

According to a fourth aspect of the present invention, a method of sterilizing a member is provided, comprising positioning a member in a housing defining an enclosure therein for receiving and holding the member, and turning on a first source of ultraviolet light, which is positioned in the enclosure for illuminating the member and interface device for a fibre optic probe with ultraviolet light.

The fibre optic probe is connected to the interface device at a first end of the fibre optic probe for enabling the fibre optic probe to receive the ultraviolet light such that the ultraviolet light is able to be transmitted along the fibre optic probes.

The fibre optic probe and a cleaning head are introduced into the internal parts of the member, and the cleaning head is positioned at a second end portion of the fibre optic probe.

Both the apparatuses and the methods described above provide an improved sterilization of a member, because the member is saved from wear and tear caused by a short sterilization time and a low pressure and temperature (room temperature).

DETAILED DESCRIPTION OF THE INVENTION

Preferred embodiments will now be described in detail by way of examples and with references to the accompanying drawings.

Figure 1:
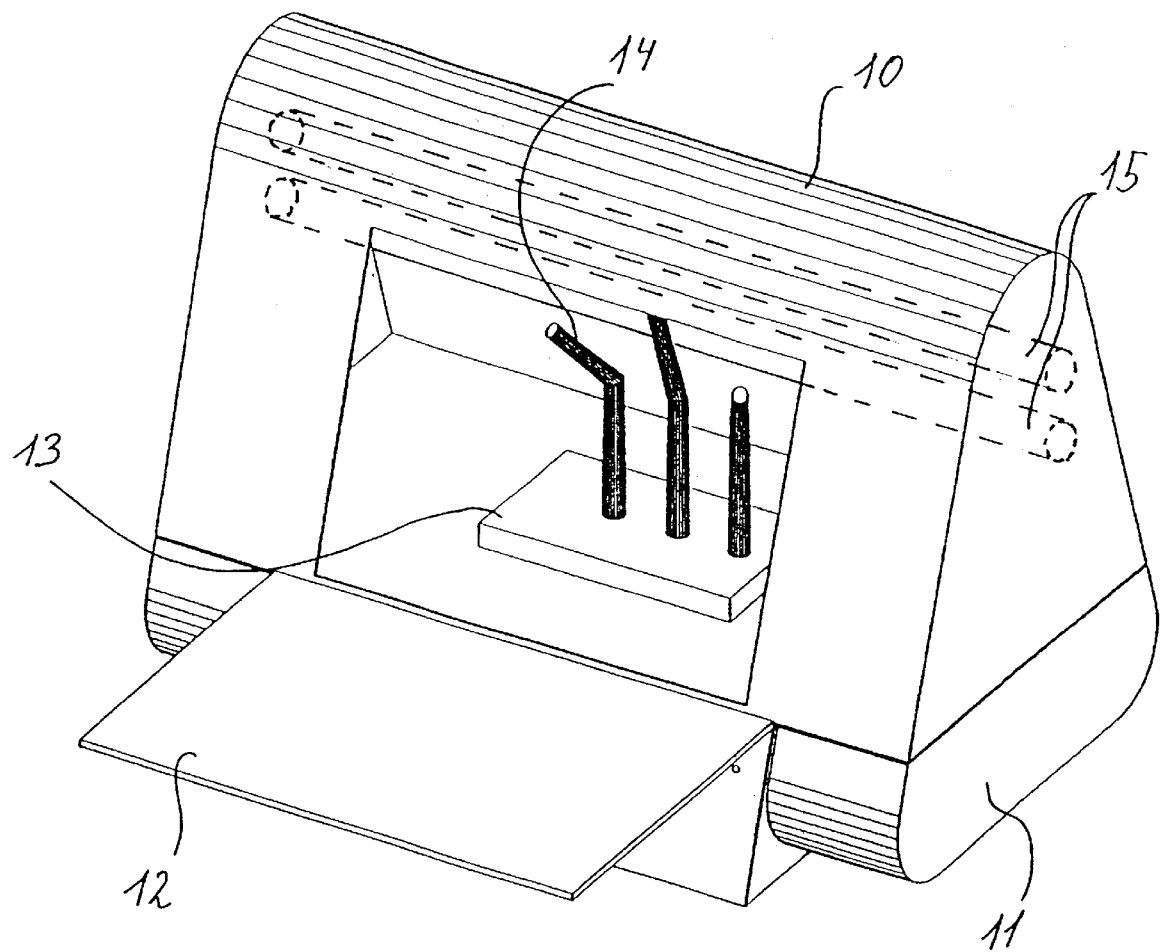
FIG. 1 shows a housing of an apparatus according to the present invention.

FIG. 1 shows a housing of an apparatus according to the present invention. The apparatus comprises a housing 10 with an enclosure defined therein, a box 11 positioned beneath the housing, a front door 12 through which the member to be sterilized is introduced into the enclosure, and a holding component 13 for receiving and holding the members to be sterilized. The members 14 to be sterilized are introduced through the front door and positioned on the holding component 13, so that the they can be illuminated by the source of ultraviolet light 15. The holding component is connected to an ozone source (not shown), so that the internal parts of the members are sterilized in their internal parts with a forced flow of ozone. The front door comprises a closing device (not shown) which closes the door tight, so that the ozone and the ultraviolet light and any other gasses or rays in the enclosure can not enter the area surrounding the apparatus.

The internal surfaces of the housing are painted with an ozone neutralizing paint, for further preventing ozone from leaving the enclosure and entering the area surrounding the apparatus. Furthermore, the internal surfaces of the housing may have a reflecting device for improving the illumination of the members to be sterilized.

Figure 2:
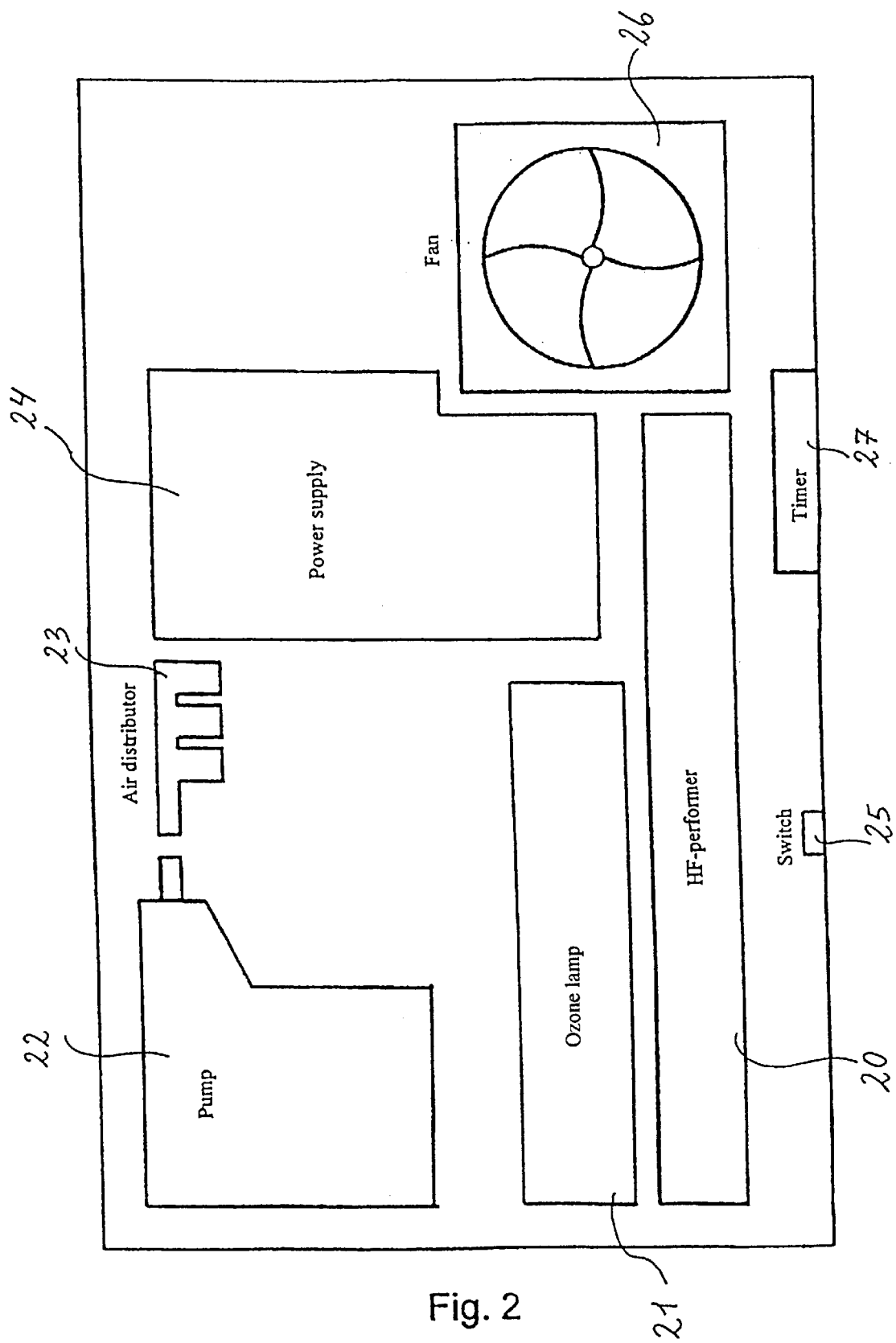
FIG. 2 shows a block diagram of major components comprised in the apparatus according to the present invention.

FIG. 2 shows a block diagram of major components of the apparatus according to the present invention. The apparatus comprises an HF-performer 20 for controlling the source of ultraviolet light (not shown) that illuminates the member. The apparatus further comprises an ozone source 21, a pump 22 for blowing atmospheric air or oxygen into the ozone source, an air distributor 23 for distributing the ozone into the several pipe stubs in the holding component (not shown), an electrical power supply 24 for supplying the components with power. A switch 25 is also provided for turning the components on or off. The apparatus also comprises a fan 26 which is positioned in a ventilating grating (not shown), so that the fan draws the ozone from the enclosure and out to the surrounding atmosphere. An active carbon filter (not shown) is connected to the fan that forces, e.g. draws, the ozone through the carbon filter, so that the ozone is transformed into oxygen.

For controlling the sterilization process, the apparatus further comprises a timer 27 which is connected to a processor (not shown), so that the time interval at which the ultraviolet light sources are switched on, may be adjusted and controlled. The processor and timer are able to control the switching on or off of all the major components in the apparatus.

Figure 3:
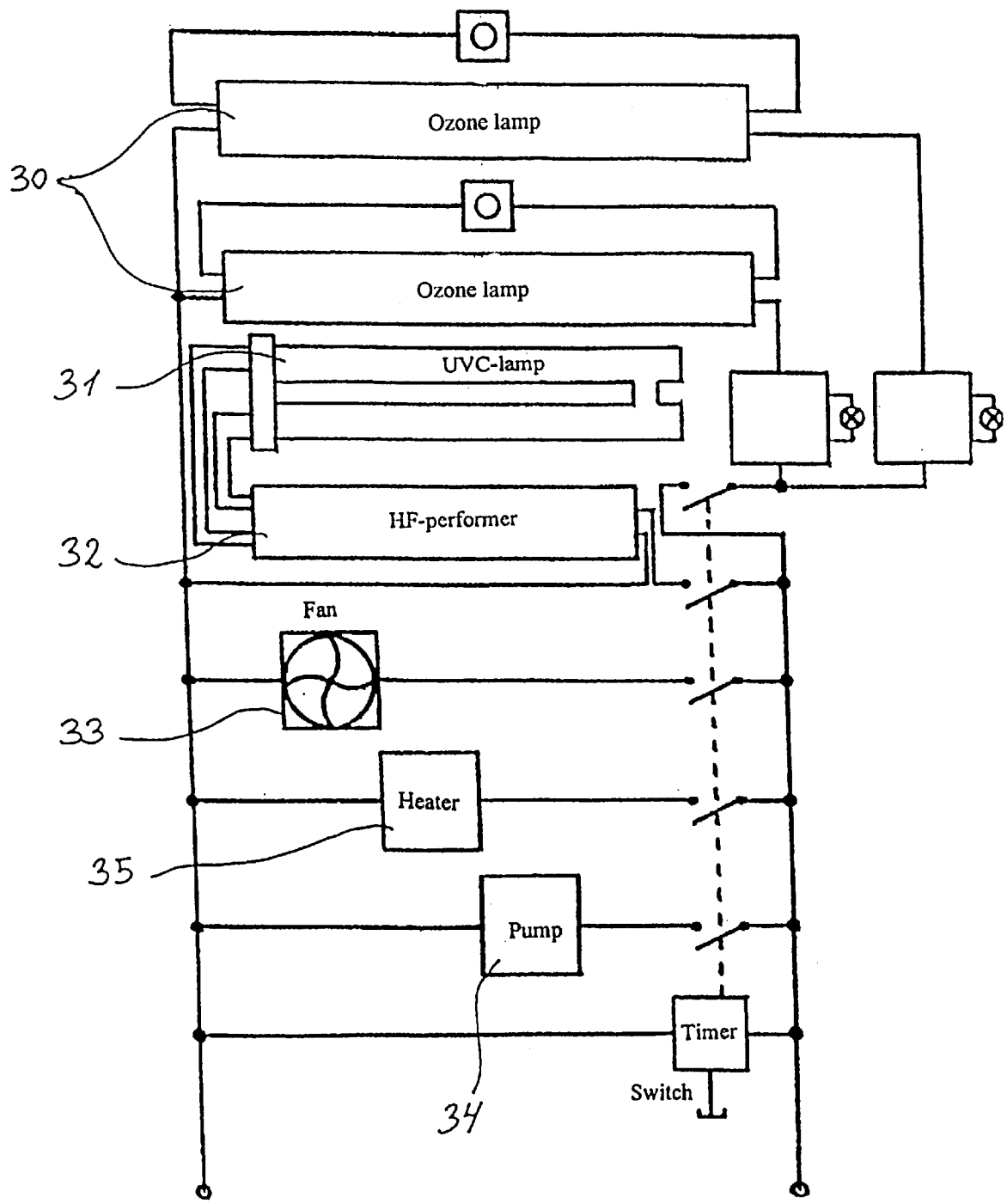
FIG. 3 is a block diagram of the electrical circuit of the apparatus according to the present invention.

FIG. 3 is a block diagram of the electrical circuit of the apparatus according to the present invention. The apparatus includes, two ozone generating sources 30 for sterilizing the member, a source of ultraviolet light 31 for illuminating the member, an HF-performer 32 which controls the source of ultraviolet light, a fan 33 positioned in the ventilation grating (not shown), a pump 34 for blowing atmospheric air or oxygen into the ozone generating source, and a heater 35. The heater 35 heats the forced flow of ozone before it is blown into the internal parts of the member to be sterilized. By heating up the forced flow of ozone, the activity of the ozone molecules is increased so that an improved sterilization of surfaces, such as internal surfaces, of the member can be accomplished. The apparatus further comprises the switch and timer as shown in FIG. 2.

Figure 4:
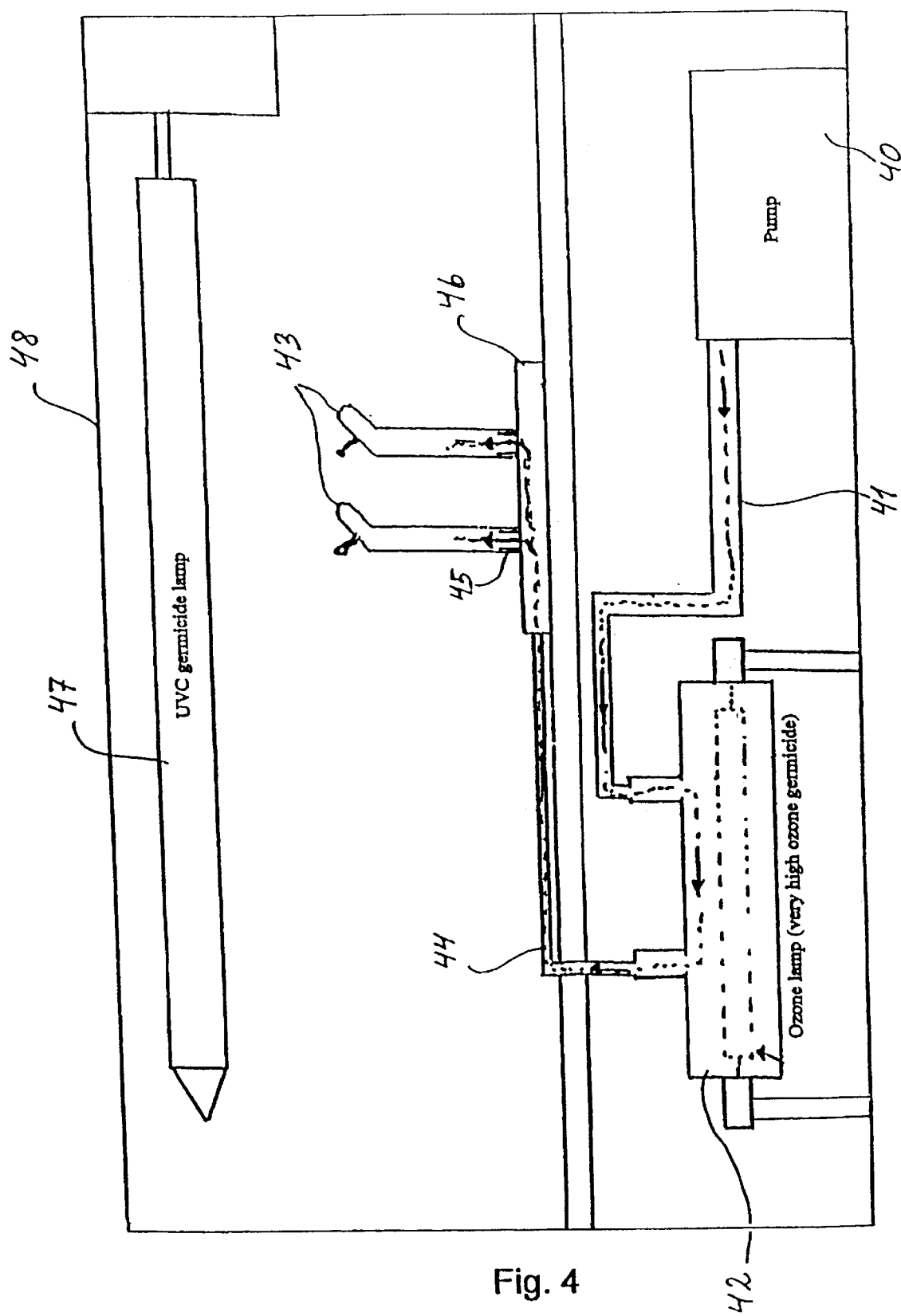
FIG. 4 illustrates schematically the operation of an apparatus according to the present invention.

FIG. 4 illustrates schematically the operation of an apparatus according to the present invention. The operation comprises blowing atmospheric air or oxygen through a pump 40, the pump being connected via tubes 41 to the ozone generating source 42. In the ozone generator, the oxygen of the atmospheric air or pure oxygen is transformed into ozone by illuminating the air or oxygen with ultraviolet light having a wavelength of approximately 183.7 nm. From the ozone generator, the ozone is blown into the internal parts of the members 43 to be sterilized via tubes 44 and the pipe stubs 45 on the holding component 46. For sterilizing the outer surface of the members 43, the members are illuminated with ultraviolet light from an ultraviolet light source 47 (a UVC germicide lamp). The source emits ultraviolet light having a wavelength of approximately 253.7 nm. All the components are arranged in the housing 48.

Figure 5:
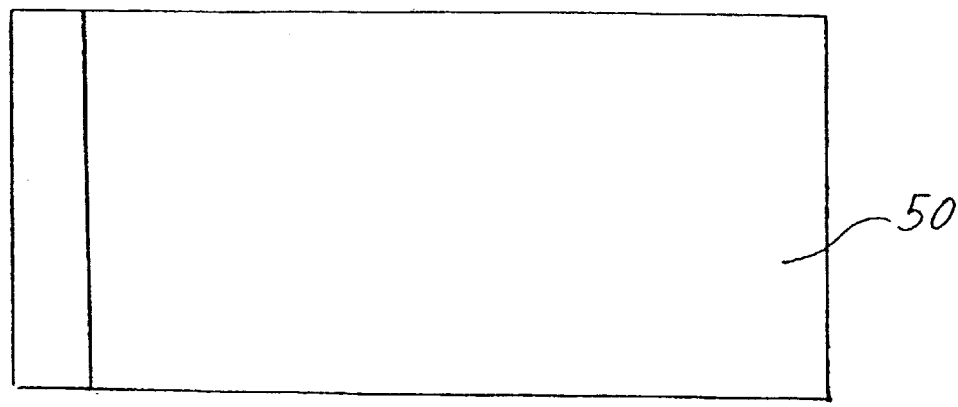
FIG. 5 shows a sealed bag according to the present invention.
Figure 5:
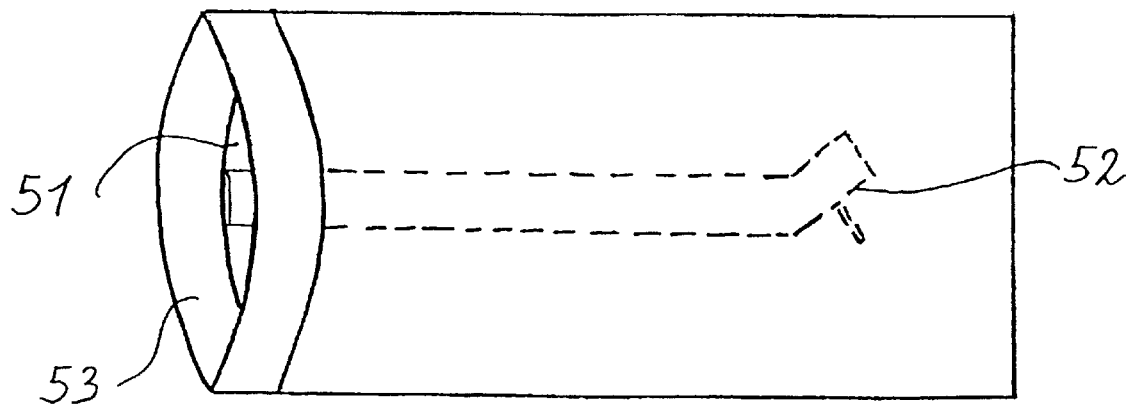
Figure 5:
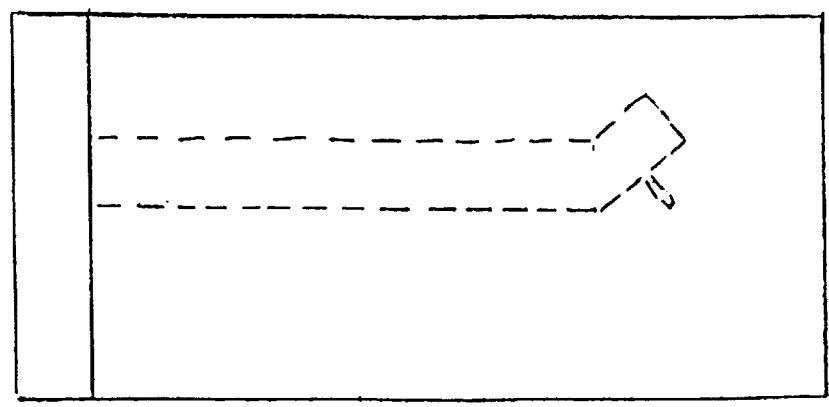

FIG. 5 shows a sealed bag according to the invention. The bag 50 has an opening 51 in the bottom part of the bag, so that the bag may be pulled over the member 52. The bag is made of a material which is penetrable by ultraviolet light, so that the member can be sterilized on the outer surfaces while being covered by the bag. The closing device 53 which is provided around the opening keeps the bag substantially closed while the member is positioned on the holding component. When removing the member from the holding component, the member remains in the bag and the closing device will close the bag, so as to prevent the member from contacting the surrounding atmosphere and/or to prevent human contact.

Figure 6:
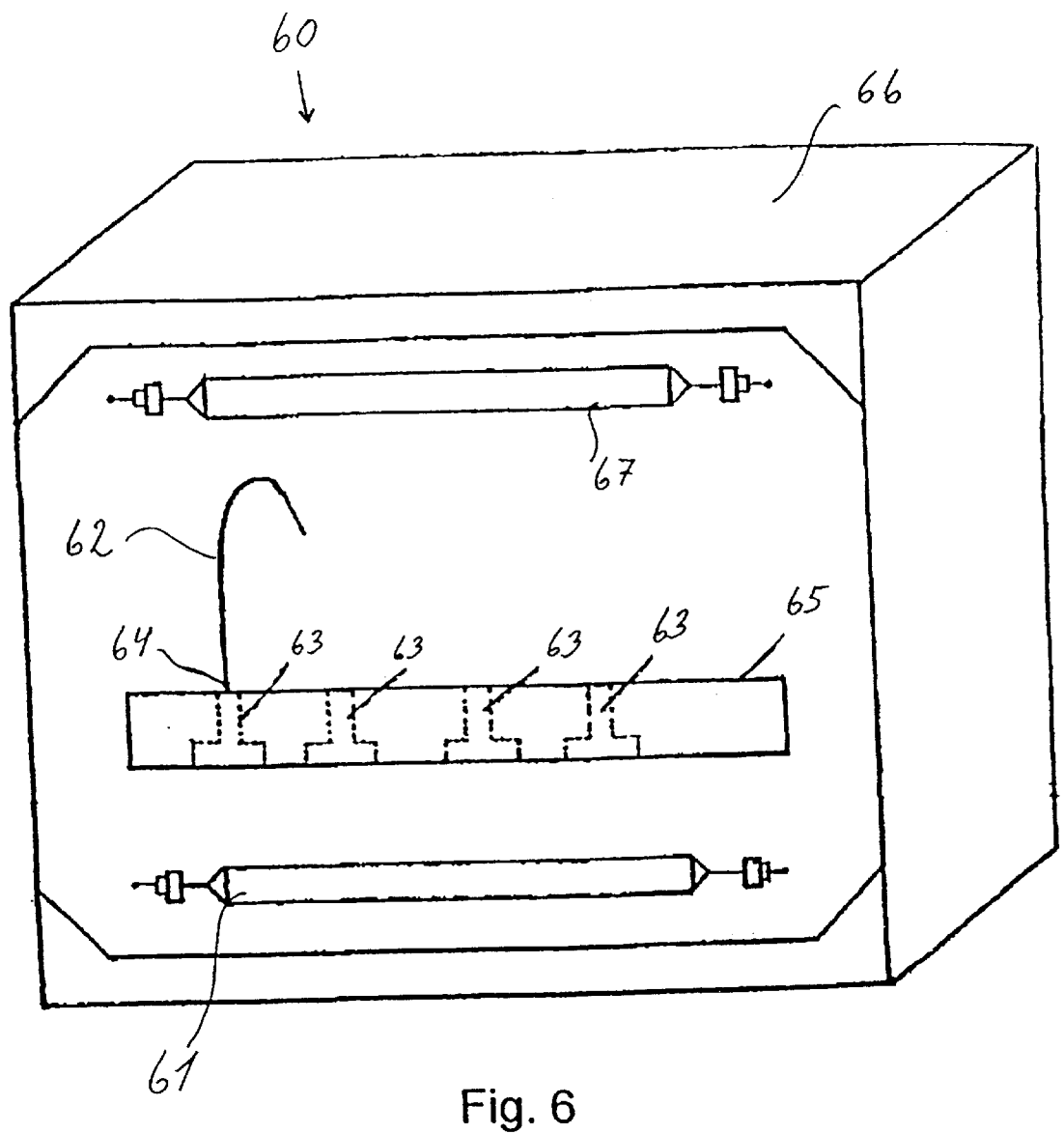
FIG. 6 shows another embodiment of the present invention.

FIG. 6 shows another embodiment of the invention. The apparatus 60 comprises a source of ultraviolet light 61, and a fibre optic probe 62. The interface device 63 is provided at a first end 64 of the fibre optic probe 62. The interface device 63 allows the fibre optic probe 62 to receive the ultraviolet light from the source 61 such that the ultraviolet light is able to be transmitted along the fibre optic probe 62.

The interface device 63 has an inverted T-shape, and a plurality of the interface devices 63 may be provided in the holding component 65. The holding component 65 is positioned in a housing 66 which contains both the UV source 61 and the fibre optic probe 62. The holding component may be of any suitable and appropriate size and shape 25 for receiving any suitable and appropriate type of member to be sterilized.

The apparatus 60 is such that each fibre optic probe 62 is able to sterilize inner parts of the member. Additionally, the apparatus is able to sterilize the outside of the member. This is effected using the source 61 and the source 67 of ultraviolet light. The ultraviolet light from the sources 61 and 67 is able to illuminate the outside of the member and thereby sterilize the outside of the member.

Figure 7:
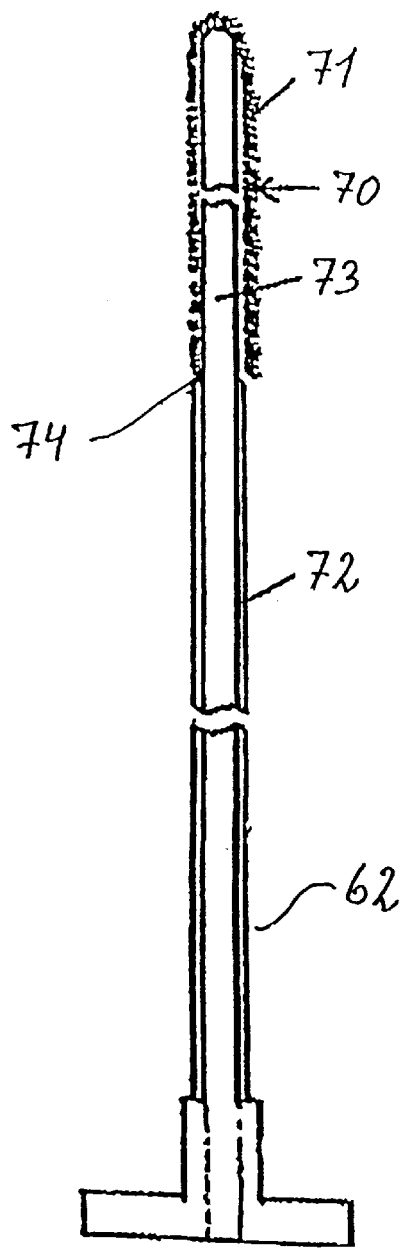
FIG. 7 shows a fibre optic probe according to the present invention.

FIG. 7 shows a fibre optic probe according to the present invention. As shown, the cleaning head 70 has a cross sectional size which is substantially the same as the cross sectional size of the fibre optic probe 62 shown in FIG. 6. The cleaning head 70 comprises a reflecting device 71 for reflecting the ultraviolet light from the cleaning head 70 which is positioned at the second end 74 of the fibre optic probe 62. The fibre optic probe 62 has an outer covering 72. This outer covering is removed at the cleaning head 70, so that an optical fibre 73 running along the center of the fibre optic probe 62 is exposed. The reflecting device 71 is in direct contact with the optical fibre 73. The reflecting device 71 is a plurality of small polished steel mirrors.

Figure 8:
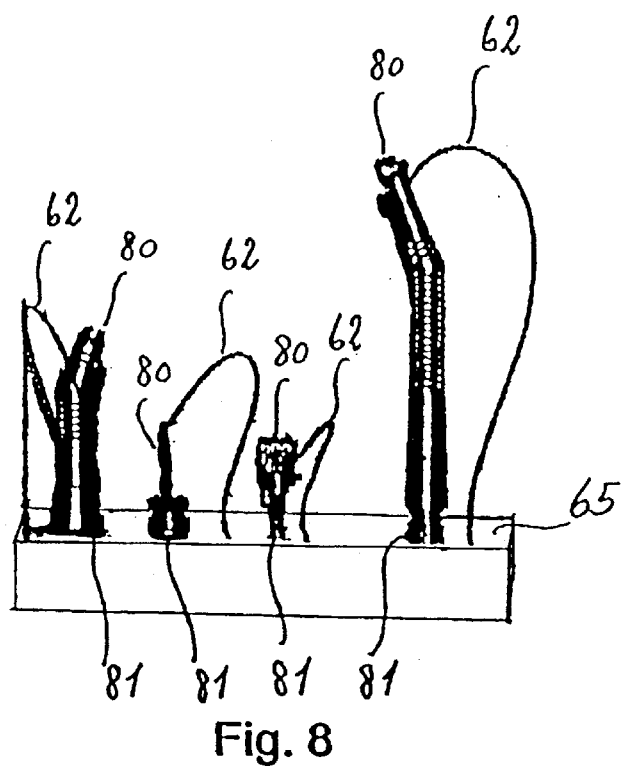
FIG. 8 shows a holding component with members to be sterilized and fibre optic probes according to the present invention.

FIG. 8 shows a holding component with members to be sterilized and fibre optic probes according to the present invention. The holding component 65 comprises receiving device such as small pipe stubs 81 for receiving the members 80. As shown, the holding component is able to receive different kinds of members to be sterilized. Each member may be sterilized with a single fibre optic probe as shown in FIG. 6, or alternatively, a plurality of separate fibre optic probes 62 as shown in FIG. 3.

The illustrations of FIGS. 6–8 are only examples of the present invention. Therefore modifications may be effected. Thus, for example, a reflecting device 71 other than the polished steel mirrors may be employed. The apparatus 60 may be such that the housing 66 has a different shape, such as the one shown in FIG. 1. If desired, there may be only one source of ultraviolet light for both the fibre optic probe 62 and also for the outside of the member 80. Alternatively, more than two sources of the ultraviolet light may be employed. The source 67 may be replaced by an ozone generating source. The source 61 may be a source that produces ultraviolet light and ozone like a UVC-lamp. A source of ozone may be provided which is additional to the sources 61 and 67.

What is claimed is:

1. An apparatus for sterilizing a member, comprising:

a housing having an enclosure defined therein for receiving and holding the member in said enclosure;

an ultraviolet light source arranged in said enclosure so as to illuminate the member with ultraviolet light;

an ozone source for generating ozone to be brought into contact with at least internal surfaces of the member for sterilization of the contacted surfaces;

an ozone pump connected to said ozone source for generating a flow of ozone within said enclosure; and a heating component for heating the ozone before the ozone enters the member to be sterilized.

2. The apparatus of claim 1, further comprising a holding component in said enclosure, said holding component being operable to receive and hold the member.

3. The apparatus of claim 2, wherein said holding component is connected to said ozone pump so that the ozone flow generated by said ozone pump passes internal surfaces of the member.

4. The apparatus of claim 1, wherein said ultraviolet light source comprises a first ultraviolet light source, said ozone source including a second ultraviolet light source for generating ozone.

5. The apparatus of claim 4, further comprising a processor for controlling an operation of said first ultraviolet light source, said ozone source including said second ultraviolet light source, said ozone pump, and said heating component, said processor being operable to start and stop said first ultraviolet light source, said second ultraviolet light source, and said ozone pump, and being operable to control a sterilization process such that:

said first ultraviolet light source is turned on for approximately 30 seconds;

said ozone source is turned on for approximately 30 seconds; and ozone within said enclosure is transformed into oxygen to prevent emission of ozone to an area surrounding said apparatus.

6. The apparatus of claim 1, wherein said apparatus is operable to reduce the number of living microorganisms on the member by a factor of at least $10^6$.

7. The apparatus of claim 1, wherein said apparatus is operable to sterilize the member such that the member has less than $10^5$ living microorganisms thereon after sterilization.

8. The apparatus of claim 1, wherein said apparatus is operable to sterilize the member such that the member has less than $10^4$ living microorganisms thereon after sterilization.

9. The apparatus of claim 1, further comprising a sealable bag for covering the member so as to protect the member from the surrounding atmosphere and human contact during handling before and after sterilization.

10. The apparatus of claim 1, wherein said housing has inner walls coated with an ozone-neutralizing paint.

11. The apparatus of claim 1, further comprising a carbon filter for transforming ozone into oxygen.

* * * * *